United States Patent [19]

Uemura et al.

[11] Patent Number: 4,721,777

[45] Date of Patent: Jan. 26, 1988

[54] PROCESS FOR THE VIRUS-INACTIVATION OF IMMUNOGLOBULIN

[75] Inventors: Yahiro Uemura, Hirakata; Katuhiro Uriyu, Sakurai; Tsuyoshi Takahashi, Toyonaka; Takashi Goto, Kyoto; Masahiro Funayama, Hirakata; Masayuki Nishida, Nagaokakyo; Tadakazu Suyama, Kyoto, all of Japan

[73] Assignee: The Green Cross Corporation, Osaka, Japan

[21] Appl. No.: 778,708

[22] Filed: Sep. 23, 1985

[30] Foreign Application Priority Data

Sep. 25, 1984 [JP] Japan ................................. 59-200241

[51] Int. Cl.⁴ .............................................. C07K 3/12
[52] U.S. Cl. ..................................... 530/389; 530/387; 530/412; 530/418; 530/427; 424/85; 424/101
[58] Field of Search ............... 530/387, 389, 412, 418, 530/427; 424/85, 101

[56] References Cited

U.S. PATENT DOCUMENTS

| | | | |
|---|---|---|---|
| 4,327,086 | 4/1982 | Fukushima et al. | 424/101 |
| 4,440,679 | 4/1984 | Fernandes et al. | 530/383 |
| 4,446,134 | 5/1984 | Naito et al. | 530/383 |
| 4,590,002 | 5/1986 | Zalton et al. | 530/387 |

FOREIGN PATENT DOCUMENTS

| | | |
|---|---|---|
| 0035204 | 9/1981 | European Pat. Off. . |
| 0094611 | 3/1983 | European Pat. Off. . |
| 0124506 | 4/1984 | European Pat. Off. . |
| 0159311 | 2/1985 | European Pat. Off. . |
| 58-500548 | 4/1983 | Japan . |
| 58-213721 | 12/1983 | Japan . |

OTHER PUBLICATIONS

Rahn, Physical Methods of Sterilization of Microrganisms, pp. 1–36.

*Primary Examiner*—Morton Foelak
*Assistant Examiner*—Garnette D. Draper
*Attorney, Agent, or Firm*—Cushman, Darby & Cushman

[57] ABSTRACT

Virus-contaminated immunoglobulin can be virus-inactivated by heating it in a substantially dry state at a temperature of 30° to 100° C. for a period of time sufficient for inactivating virus with maintaining original activity of the immunoglobulin. The addition of glycine, sodium chloride, sodium acetate, polyethylene glycol, albumin or mannitol enhances the effect and gives good solubility and good state to the solution of the virus-inactivated immunoglobulin.

14 Claims, No Drawings

PROCESS FOR THE VIRUS-INACTIVATION OF IMMUNOGLOBULIN

This invention relates to a process for heat-treating immunoglobulin to inactivate the virus possibly present therein.

The most reliable method heretofore used for treating plasma protein such as albumin to inactivate the virus which possibly contaminates the protein is to heat-treat it in the state of its aqueous solution (hereinafter referred to as "liquid heating method"), which is based on the report of Murray et al. [The New York Academy of Medicine, 31 (5), 341–358 (1955)]. The method has been widely used through many years up to the present and the effect of inactivating viruses of the liquid heating method has been substantiated also epidemilogically.

However, only a limited kind such as albumin of plasma proteins can withstand the liquid heating. Particularly, those plasma proteins which have physiological or biological activities are very sensitive to heat, susceptible to thermal denaturation, and liable to undergo the decrease or disappearance of the activities.

On the other hand, apart from the liquid heating method, it has been revealed from experiments conducted using a blood coagulation enzyme such as factor VIII as the model of plasma protein that when the heat treatment of the enzyme is conducted in a dry state wherein little moisture is contained therein (hereinafter referred to as "dry heat treatment") the lowering of its activity can be markedly suppressed as compared with that in the liquid heating method. In this respect reference is made to Japanese Patent Application (Laid-Open) No. 213,721/83 (priority: May 13, 1983 based on U.S. Ser. No. 377,863) concerning factors I and VIII.

As for a stabilizer for plasma proteins which is used in the liquid heating method, it is reported that the stabilizer such as albumin, glycine, mannitol or sorbitol does not affect on the stability of the blood coagulation enzyme but gives good solubility and clarity to an aqueous solution of the virus-inactivated enzyme after the heat treatment. (Japanese Patent Application Kohyo (Laid-Open under national phase of PCT application) No. 500,548/83 corresponding to PCT/US82/00366, concerning factors II, VIII, IX and X.

In the meantime, as to the mechanism of the inactivation of viruses by heating, it has been reported that whereas the virus is inactivated based mainly on the denaturation of the protein component of the virus in the liquid heating, the virus is injured and deprived of its pathogenicity owing mainly to the oxidation of the lipid component of the virus in the dry heat treatment; and it is suggested that even if the mechanism of inactivation of viruses in above-mentioned two kinds of heat treatment overlap in some parts, basically they are different from each other [Rahn, Physical Methods of Sterilization of Microorganisms, Bact. Rev., 9, 1–47 (1945)].

An object of this ihvention is to provide a dry heat treatment of immunoglobulin, which can inactivate viruses present therein without inactivating the immunoglobulin itself.

The present inventors have found that viruses present in immunoglobulin can be inactivated without losing the activity of the globulin by dry-heat treating the globulin and that when the dry heat treatment of immunoglobulin is conducted in the presence of a stabilizer the globulin is markedly stabilized further and the immunoglobulin dry-heat treated under such conditions shows good solubility in water and good state of solution. This invention has been accomplished on the basis of these findings.

Thus, this invention relates to a process for heat-treating immunoglobulin which comprises heating immunoglobulin contaminated with a virus in a substantially dry state, preferably in the presence of a specified stabilizer, until the virus becomes inactivated, whereby the contaminant virus is inactivated and the solubility in water and the stability of the immunoglobulin are improved.

The immunoglobulins which are the subject of the heat treatment of this invention are those which have biological or physiological activities characteristic of immunoglobulin, for example, those which can be obtained by the fractionation of plasma proteins.

Examples of such immunoglobulins include those of human, horse and mouse origin. These may be either a polyclonal antibody or a monoclonal antibody and are preferably IgG, IgA or IgM.

This invention is usually carried out by lyophilizing an immunoglobulin solution and then heating the lyophilized product in substantially dry state, that is, a state with as small moisture content as possible, preferably at 3% or less, and usually 0.05 to 3%.

The temperature used in the present dry heat treatment is usually 30° to 100° C., most preferably about 60°, and the heating time is one sufficient for inactivating the virus only, and it is usually 10 minutes to 200 hours depending on the temperature used, and preferably about 10 to 100 hours.

The viruses which are to be the object of the inactivation by heat treatment of this invention are those which are suspected of contaminating human plasma proteins, such as, particularly, the hepatitis virus.

The stability of immunoglobulin in the heat treatment of this invention can be further enhanced by conducting the treatment in an inert gas atmosphere. Examples of the inert gas include nitrogen, argon and helium.

It has been found that on the contrary to the disclosure of the reference already mentioned, concerning a blood coagulation enzyme, in case of an immunoglobulin the lowering of the activity is unavoidable in the dry heat treatment and the addition of a stabilizer including some ones known effective in the liquid heating method is effective for maintaining the activity as it is before heating. It gives also good solubility and good state of solution to the resulting virus-inactivated product, as the reference states.

The stabilizer used in this invention is at least one member selected from glycine, an alkalimetal chloride such as sodium chloride, an alkalimetal acetate such as sodium acetate, polyethylene glycol, albumin and mannitol.

The stabilizer is used, for example, in an amount corresponding to the concentration thereof of about 0.01 to 4% (w/v) relative to 0.01 to 2% (w/v) immunoglobulin solution in the case of monoclonal immunoglobulin and relative to 2 to 8% (w/v) immunoglobulin solution in the case of polyclonal immunoglobulin. The stabilizing effect, the solubility in water and the state of solution are most well balanced for making the immunoglobulin into a medical preparation when the amount of the stabilizer added is in the above-mentioned range.

The symbol "% (w/v)" means herein the amount of a solute by weight (gram) in 100 ml of the resulting solution.

The immunoglobulin is usually used in a substantially dried, lyophilized state and the stabilizer is preferably added to an immunoglobulin solution prior to the lyophilization treatment thereof.

Though the stabilizer may be removed after the dry heat treatment of this invention from the immunoglobulin preparation, it may be left incorporate therein as far as permitted.

Further, there is little correlation between the degree of purification of immunoglobulin and its heat resistance, and the stabilizing effect of a stabilizer does not vary with the extent of purification of the immunoglobulin used. Accordingly, though the heat treatment of this invention is preferably carried out with respect to a fraction or a composition containing purified immunoglobulin so as to be administered to a patient, it may be conducted at any step of the purification of the immunoglobulin.

Since the process of this invention enables the inactivation of viruses, which may possibly contaminate an immunoglobulin preparation, without losing much of the activity of immunoglobulin, a precious plasma protein, it is useful as an industrial process for producing the plasma protein preparation.

This invention will be described in detail below with reference to Experimental Examples and Examples, but it is in no way limited thereto.

EXAMPLE 1

Fr-II (IgG fraction) was obtained from normal human plasma by means of the Cohn's cold alcohol fractionation method. One kg of the Fr-II paste thus obtained was dissolved in 1.5 l of cold water and then mixed with 15 g of glycine. The resulting IgG solution (5% w/v) was adjusted to a pH of 6.3 to 6.5 and then lyophilized. The moisture content after the lyophilization was 0.8%. The lyophilized IgG powder was heat-treated at 60° C. for 72 hours. The product thus obtained was examined for test items of solubility, HBsAg antibody titer, measles antibody titer, anti-diphtherial toxin titer, electrophoresis using a cellulose acetate membrane, and gel filtration in comparison with the IgG before the heat treatment. The results have revealed that no marked change is observed in any of these items and human IgG is stable under the above-mentioned heat treatment conditions.

EXAMPLE 2

Fr-III fraction obtained from normal human plasma by the Cohn's cold alcohol fractionation method was purified by the method of salting-out or fractionation using acrinol. A 5% (w/v) solution of the human IgA thus obtained was mixed with glycine to its final concentration of 1% (w/v), and sodium chloride to that of 0.5% (w/v), and the mixed solution was lyophilized. The moisture content of the lyophilized powder was 2% or less. The powder was heated at 60° C. for 72 hours and then examined for its solubility, IgA concentration, measles antibody titer, and electrophoresis, using a cellulose acetate membrane. The test results were compared with those obtained with the powder before the heating and revealed that the powder was stable also after the heat treatment.

EXAMPLE 3

To a 0.1% (w/v) solution of a mouse monoclonal antibody against anti-human lymphoblasts belonging to the IgM class was added human albumin to its final concentration of 1% (w/v), sodium chloride to that of 0.45% (w/v), mannitol to 2% (w/v) and Polyethylene Glycol 4000 to 0.1% (w/v), and then the mixture was lyophilized to a substantially dry state, and further heated at 60° C. for 72 hours.

The antibody titer against human lymphoblasts and the solubility of the lyophilized products were tested both before and after the heat treatment. The results have revealed that 75% of the antibody titer remains and the solubility shows no change after the above-mentioned heat treatment.

EXAMPLE 4

To a 2% (w/v) aqueous solution of mouse monoclonal antibodies against established human cancer cells (MKN-45) belonging to the IgG class, was added sodium chloride to a final concentration of 0.6% (w/v) and mannitol to that of 1% (w/v), and the resulting solution was lyophilized to a substantially dry state. Then the lyophilized product was heated at 60° C. for 72 hours. The solubility and the antibody titer were tested with the lyophilized product before and after the heat treatment and the results have revealed that they are not changed by the above-mentioned heat treatment.

EXAMPLE 5

To a 5% (w/v) aqueous solution of horse polyclonal antibodies against human lymphocytes belonging to the IgG class, was added sodium chloride to a final concentration of 0.7% (w/v) and glycine to that of 1% (w/v). The resulting solution was lyophilized to a substantially dry state, and further heated at 60° C. for 72 hours. The product was examined in the same manner as in Example 4 and the results have revealed that the examined properties are not changed by the above-mentioned heat treatment.

EXAMPLE 6

In the same manner as that disclosed in Japanese Patent Application Kokai (Laid-Open) No. 72526/83, human monoclonal antibodies against HBsAg belonging to the IgG class were produced by using human B-lymphocytes transformed with EB-viruses. To aqueous, 1% (w/v) solution of the antibody was added sodium chloride to a final concentrration of 1% (w/v). The mixture was lyophilized and then heated at 70° C. for 30 hours. The test results of the HBs antibody titer have revealed that it is not changed by the above-mentioned heat treatment.

EXPERIMENTAL EXAMPLE 1

(Kind of stabilizer)

To a 5% (w/v) solution of Fr-II (IgG fraction) prepared in the same manner as in Example 1, was added the stabilizer listed in Table 1 each to a final concentration of 0.5% (w/v). The resulting solution was adjusted to a pH of 6.3 to 6.5 and then lyophilized to a substantially dry state. The IgG powder thus obtained was heat-treated at 60° C. for 72 hours and then examined for the solubility, anti-diphtherial toxin titer and measles antibody titer. The results are shown in Table 1. The tests were conducted according to "THE STANDARD FOR BIOLOGICAL MEDICAL PREPARATIONS" (p. 207–209, published by SAIKIN SEIZAI KYOKAI, 1979).

The results have revealed that the stability is improved by the use of the stabilizer as compared with the case where no stabilizer is added (control). The stabilizing effect was similar both in the single use of a stabilizer and in the joint use of two or more stabilizers. Further, no particular difference in the effect was observed with difference in the mixing ratio of jointly used stabilizers.

EXPERIMENTAL EXAMPLE 2

(Amount of stabilizer to be added)

To a 5% (w/v) aqueous solution of Fr-II (IgG fraction) prepared in the same manner as in Example 1, was added the stabilizer listed in Table 2 each in an amount indicated in the Table. The resulting solution was adjusted to a pH of 6.3 to 6.5 and then lyophilized. The procedures thereafter were similar to those in Experimental Example 1. The results obtained are shown in Table 2.

The results have revealed that the effective amount of the stabilizer is 0.01 to 2% (w/v) relative to the aqueous solution of the IgG fraction. The effective amount was the same irrespective of whether the stabilizers were used each alone or in combination.

TABLE 1

| Stabilizer | | B | C | D |
|---|---|---|---|---|
| Fr-II (standard): Before heat treatment | | | 3-4 | 27 |
| No addition (Control) | | x | 2-3 | 20 |
| Single use | | | | |
| Glycine | | o | 3-4 | 28 |
| Sodium chloride | | o | 3-4 | 26 |
| Sodium acetate | | o | 3-4 | 25 |
| Polyethylene glycol 4000 | | o | 3-4 | 26 |
| Albumin | | o | 3-4 | 28 |
| Mannitol | | o | 3-4 | 26 |
| Joint use | | | | |
| Glycine/Polyethylene glycol 4000 | (1:1) | o | 3-4 | 27 |
| Glycine/Polyethylene glycol 4000 | (1:2) | o | 3-4 | 26 |
| Glycine/Polyethylene glycol 4000 | (2:1) | o | 3-4 | 28 |
| Sodium acetate/Albumin | (2:1) | o | 3-4 | 26 |
| Sodium chloride/Mannitol | (1:3) | o | 3-4 | 26 |
| Glycine/Polyethylene glycol 4000/Sodium chloride | (1:1:1) | o | 3-4 | 27 |

TABLE 2

| Stabilizer | | A | B | C | D |
|---|---|---|---|---|---|
| Fr-II (Standard) | | | | 3-4 | 27 |
| No addition (Control) | | 0 | x | 2-3 | 20 |
| Single use | | | | | |
| Glycine | | 0.001 | x | 2-3 | 22 |
| | | 0.01 | Δ | 3-4 | 22 |
| | | 0.1 | o | 3-4 | 26 |
| | | 1.0 | o | 3-4 | 26 |
| | | 2.0 | o | 3-4 | 27 |
| | | 5.0 | Δ | 3-4 | 27 |
| Polyethylene glycol 4000 | | 0.001 | x | 2-3 | 22 |
| | | 0.01 | o | 3-4 | 27 |
| | | 1.0 | o | 3-4 | 27 |
| | | 5.0 | x | 2-3 | 20 |
| Joint use | | | | | |
| Sodium chloride/Mannitol | (1:1) | 0.001 | x | 2-3 | 20 |
| | | 0.01 | o | 3-4 | 26 |
| | | 0.1 | o | 3-4 | 26 |
| | | 1.0 | o | 3-4 | 27 |
| | | 2.0 | o | 3-4 | 27 |
| | | 5.0 | Δ | 3-4 | 22 |
| Glycine/Sodium acetate | (3:1) | 0.01 | o | 3-4 | 27 |
| | | 0.1 | o | 3-4 | 27 |
| Sodium chloride/Polyethylene glycol 4000/Albumin | (1:1:1) | 0.01 | o | 3-4 | 27 |
| | | 0.1 | o | 3-4 | 27 |

Note:
A: Amount of stabilizer added [% (w/v)]
B: Solubility (o: Easily soluble; Δ: Some insolubles; x: Many insolubles)
C: Anti-diphtherial toxin titer (IU/100 mg)
D: Measles antibody titer (IU/100 mg)

What is claimed is:

1. A process for virus-inactivating immunoglobulin comprising heating a composition containing the immunoglobulin in a substantially dry state at a temperature of 30° to 100° C. for a period of time sufficient to inactivate virus contained in the composition without destroying the activity of the immunoglobulin itself.

2. A process according to claim 1, wherein the composition contains a stabilizer selected from the group consisting of glycine, alkalimetal chloride, alkalimetal acetate, polyethylene glycol, albumin and mannitol in an amount sufficient to stabilize the immunoglobulin.

3. A process according to claim 1, wherein the composition subjected to said heating comprises purified immunoglobulin suitable for administration to a patient.

4. A process according to claim 1, wherein the composition is lyophilized to the substantially dry state before said heating.

5. A process according to claim 1, wherein the composition as heated has a moisture content of 3% or less.

6. A process according to claim 1, wherein the immunoglobulin is of human, horse or mouse origin.

7. A process according to claim 6, wherein the immunoglobulin of human or mouse is a polyclonal or a monoclonal antibody.

8. A process according to claim 1, wherein the immunoglobulin is IgG, IgA or IgM.

9. A process according to claim 2, wherein the stabilizer is selected from the group consisting of alkalimetal chloride and alkalimetal acetate.

10. A process according to claim 9, wherein the alkalimetal is sodium.

11. A process according to claim 2, wherein the amount sufficient for stabilizing immunoglobulin corresponds to a concentration of the stabilizer of 0.01 to 4% (w/v) relative to 0.01 to 2% (w/v) solution of monoclonal immunoglobulin or 2 to 8% (w/v) solution of a polyclonal immunoglobulin.

12. A process according to claim 2, wherien the stabilizer is added to a solution of the composition after which the composition is lyophilized to the substantially dry state before it is heated to inactivate virus.

13. A virus-inactivated immunoglobulin prepared according to the process of claim 2.

14. A process according to claim 1 for inactivating any virus present in immunoglobulin which comprises adding a stabilizing amount of glycine to a solution of the immunoglobulin; lyopilizing said solution to a moisture content of 0.05 to 3%; and then heating the lyophilized composition for a period of 10–100 hours at about 60° C. to inactivate any virus without inactivating the immunoglobulin, the thus-treated immunoglobulin demonstrating improved stability and water-solubility.

* * * * *